United States Patent
Ding et al.

(10) Patent No.: US 7,038,088 B2
(45) Date of Patent: May 2, 2006

(54) HYDROGENATION OF HIGHLY CONTAMINATED METHYLENEDIANILINE

(75) Inventors: Hao Ding, Macungie, PA (US); Gamini Ananda Vedage, Bethlehem, PA (US); William R. Martine, Allentown, PA (US); Vipul P. Dholakia, Macungie, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/848,766

(22) Filed: May 19, 2004

(65) Prior Publication Data
US 2005/0261525 A1    Nov. 24, 2005

(51) Int. Cl.
*C07C 209/72*    (2006.01)
(52) U.S. Cl. ...................................... 564/451
(58) Field of Classification Search ................. 564/451
See application file for complete search history.

(56) References Cited

U.S. PATENT DOCUMENTS

| | | | |
|---|---|---|---|
| 2,606,925 A | 8/1952 | Whitman | |
| 2,606,927 A | 8/1952 | Barkdoll et al. | |
| 3,636,108 A | 1/1972 | Brake | |
| 3,697,449 A | 10/1972 | Brake | |
| 3,959,374 A | 5/1976 | Brennan et al. | |
| 3,959,376 A | 5/1976 | Trapasso | |
| 4,754,070 A | 6/1988 | Casey et al. | |
| 4,946,998 A * | 8/1990 | Casey et al. | 564/451 |
| 4,960,941 A * | 10/1990 | Vedage et al. | 564/450 |
| 5,026,914 A * | 6/1991 | Jenkins et al. | 564/451 |
| 5,196,587 A * | 3/1993 | Vedage et al. | 564/451 |
| 5,360,934 A * | 11/1994 | Vedage et al. | 564/451 |
| 5,545,756 A | 8/1996 | Vedage et al. | |
| 6,184,416 B1 | 2/2001 | Ding et al. | |

FOREIGN PATENT DOCUMENTS

EP    0 335 336 A2    10/1989

* cited by examiner

*Primary Examiner*—Brian Davis
(74) *Attorney, Agent, or Firm*—Michael Leach

(57) ABSTRACT

This invention relates to a process for the catalytic hydrogenation of impurity laden methylenedianiline feedstocks commonly referred to a MDA-50 and MDA-60. The process for hydrogenating methylenedianiline containing at least 40% oligomer function by weight comprises:

contacting the feedstock with hydrogen in the presence of a rhodium/ruthenium containing catalyst system carried on a lithium aluminate support under conditions for effecting ring hydrogenation.

14 Claims, No Drawings

HYDROGENATION OF HIGHLY CONTAMINATED METHYLENEDIANILINE

BACKGROUND OF THE INVENTION

Ring hydrogenation of aromatic amines using Group 6 and Group 8 metals carried on a support is well known. Two aspects in the hydrogenation process are problematic. First, contaminants in the aromatic amine substrate can poison the catalyst thus impacting catalyst activity and catalyst life. Second, catalyst attrition can occur thereby resulting in catalyst loss and plugging of catalyst filtration equipment.

Representative patents which illustrate various processes for the hydrogenation of aromatic amines, including methylenedianiline are as follows:

U.S. Pat. Nos. 2,606,925 and 2,606,927 disclose the hydrogenation of nitroaromatics and aromatic amines. The '925 patent shows the use of ruthenium oxide as a catalyst whereas the '927 discloses the use of cobalt on alumina.

U.S. Pat. Nos. 3,636,108 and 3,697,449 disclose the hydrogenation of aromatic compounds, and particularly 4,4'-methylenedianiline, to produce a product referred to as PACM, using an alkali metal-moderated ruthenium catalyst. The catalyst is formed by depositing a ruthenium compound on a support from an aqueous solution of sodium or potassium bicarbonate, hydroxide, or the like. A wide variety of carriers such as calcium carbonate, rare earth oxides, alumina, barium sulfate, kieselguhr and the like are shown as candidate supports. The '449 patent discloses the in situ alkali moderation of the supported ruthenium catalyst using lithium hydroxide.

U.S. Pat. No. 3,959,376 discloses a process for the preparation of mixed isomeric methylene bridged polycyclohexylpolyamines by the hydrogenation of methylenedianiline feedstocks. The patentees report feed mixtures having upwards of 25% isomeric methylene diamines, i.e., feedstocks having an average functionality of from 2.0 to 3.3 can be employed if one uses a pretreatment comprising effecting an initial hydrogenation in the presence of nickel followed by hydrogenation with ruthenium.

U.S. Pat. No. 3,959,374 discloses a process for the direct hydrogenation of a methylene bridged polyphenylamine feed that contains trace impurities and oligomers. A crude MDA feed containing these impurities and oligomers is initially treated with hydrogen in the presence of a nickel catalyst prior to hydrogenation in the presence of a ruthenium catalyst.

U.S. Pat. No. 4,754,070 discloses an improved process for the hydrogenation of methylenedianiline contaminated with catalyst poisoning impurities. A catalyst comprised of rhodium and ruthenium was found to be effective in the hydrogenation of a crude methylenedianiline (MDA-85), i.e., one containing oligomers in an amount up to about 15 to 20%. Alkali moderation via addition of lithium hydroxide activation was shown to be effective for the combined catalyst. Carriers suited for the rhodium/ruthenium catalyst included alumina, carbonates, etc.

U.S. Pat. No.5,545,756 discloses a process for the hydrogenation of aromatic amines, whether mononuclear or polynuclear, using a catalyst of rhodium carried on a titania support. Examples of titania supports include $TiAl_2O_5$, $TiSiO_4$ and $TiSrO_3$. The titania support permitted the use of rhodium alone as the active metal in the hydrogenation of crude methylenedianiline. Rhodium carried on titania in combination with ruthenium on alumina was also suited as a catalyst. Lithium hydroxide addition resulted in enhanced activity.

U.S. Pat. No. 6,184,416 discloses a process for hydrogenating methylenedianiline and other aromatic amines using a catalyst comprised of rhodium and ruthenium carried on a lithium aluminate support. The hydrogenation of feedstocks of methylenedianiline and impurity laden methylenedianiline (referred to as MDA-85) wherein the feedstock contains up to about 15 to 20% of an oligomer function is described. Oligomers are three, four and five ring products.

BRIEF SUMMARY OF THE INVENTION

This invention relates to a process for the catalytic hydrogenation of high impurity laden methylenedianiline feedstocks commonly referred to as MDA-50 and MDA-60. The process for hydrogenating methylenedianiline containing at least 40% polycyclic oligomer content by weight comprises:

contacting the feedstock with hydrogen in the presence of a rhodium/ruthenium containing catalyst system carried on a lithium aluminate support under conditions for effecting ring hydrogenation.

The following represents some of the advantages that can be obtained by the use of the catalysts under specified conditions, they are:

an ability to hydrogenate a low cost methylenedianiline feedstock which is highly contaminated with large amounts of oligomer and formamide byproducts;

an ability to reuse the catalyst employed in the hydrogenation of a low cost feedstock over an extended period of time;

an ability to minimize catalyst loss and product contamination by virtue of excellent attrition resistance; and, an ability to achieve enhanced production through excellent reaction rates.

DETAILED DESCRIPTION OF THE INVENTION

Methylenedianiline is derived from nitrobenzene wherein the nitro groups are first converted to amine functionality via catalytic hydrogenation using a nickel or cobalt catalyst. The reaction product is distilled and aniline is recovered. Methylenedianiline is formed by reacting formaldehyde with the thus formed aniline in the presence of an acid catalyst resulting in a product referred to as MDA-50 and MDA-60. The methylenedianiline formed by the condensation of aniline with formaldehyde includes a large percentage of polycyclic oligomers in the form of 3, 4 and 5 rings. Initially, the 2 ring methylenedianiline product is formed but as the concentration of methylenedianiline, relative to aniline, increases in the reaction product, the formaldehyde reacts with methylenedianiline and oligomers thereof thereby extending the chain. Even in those cases where the reaction stoichiometry is controlled, approximately 40 to 50% of the reaction product is in the form of polycyclic oligomers. Also, present in the reaction product are significant levels of formamide byproducts which are poisons to ring hydrogenation catalysts.

Heretofore, in the synthesis of methylenedianiline feedstocks suited for ring hydrogenation the MDA-50 and MDA-60 reaction products are either distilled generating a 2 ring product or the reaction stoichiometry is controlled to remove or minimize oligomer formation. Subsequently, through the use of a cocatalyst of rhodium and ruthenium carried on a support of alumina and then again with lithium aluminate, it was found that a small amount of oligomer and formamide byproducts could be tolerated in the hydrogenation of a crude methylenedianiline feedstock. This feedstock was referred to as MDA-85 which contained 15–20% by weight of polycyclic oligomer function.

Summarizing, it has been common practice to generate methylenedianiline feedstocks which have less than about 20% oligomer content and low levels of catalyst poisons in the form of formamide byproducts and employ these treated feedstocks for ring hydrogenation. Feedstocks having significantly higher levels of contaminating poisons were distilled prior to effecting hydrogenation or pretreatment processes have been developed to decompose the catalytic poisons and trace amounts of impurities that poison the active metal catalysts.

Surprisingly, it has been found that one can effectively extend the hydrogenation of methylenedianiline feedstocks having approximately 85 to 90% of the 2 ring product and less than about 20% oligomer function (MDA-85) using a mixed rhodium/ruthenium catalyst carried on a lithium aluminate support to a methylenedianiline feedstock having more than 2 to 3 times the level of polycyclic oligomer impurity in MDA-85, not to mention the significantly higher levels of other catalytic impurities. For example, the formamide byproducts in MDA-85 are present in amounts less than 100 ppm whereas the formamide byproducts present in high oligomer feedstocks may be at least 0.2% and upwards to 0.6% by weight.

The methylenedianiline feedstocks employed here are commonly referred to as MDA-50 and MDA-60 where the 2-ring methylenedianiline content approximates 50% by weight and 60% by weight respectively. These feedstocks have a significantly higher level of oligomer impurities, i.e., at least 40% and generally at least 50% polycyclic oligomer by weight. It was thought these methylenedianiline feedstocks had too many oligomer impurities and catalytic poisons to allow for conversion to methylene bridged polycyclohexylpolyamines with any expectation of suitable yield and catalyst life.

In contrast to catalyst systems for the hydrogenation of substantially pure methylenedianiline and crude feedstocks contaminated with a small amount of oligomer function (MDA-85), the catalyst system is comprised of a rhodium and ruthenium metal carried on a lithium aluminate support, as opposed to the use of rhodium alone. Rhodium carried on lithium aluminate is sufficient by itself as a catalyst to hydrogenate MDA-85 but it, by itself, is not suited as a feedstock for hydrogenating high oligomer feedstocks such as MDA-50.

As stated, the catalyst system is comprised of rhodium and ruthenium. Typically, the catalyst system is comprised of a physical mixture of the two components, although both metals can present on a single support. The rhodium is present in the catalyst system in an amount, based upon its weight as metal, sufficient to provide from 0.1 to 25 weight parts rhodium per 100 weight parts of support plus metal, preferably 2 to 8 weight parts rhodium per 100 weight parts of support plus metal. Ruthenium is added to the support in an amount similar to that of rhodium. The catalyst system is formed such that the rhodium to ruthenium weight ratio is from about 1 to 20 parts rhodium per part of ruthenium. Preferably the catalyst system is comprised of from 6 to 15 weight parts rhodium/weight part ruthenium on the lithium aluminate support.

Rhodium and ruthenium are added to the support by either incipient wetness or coprecipitation in the presence of a base in water, preferred bases are LiOH, $Li_2CO_3$, or $Na_2CO_3$. The catalyst system comprised of rhodium and the lithium aluminate support is dried and heated to a temperature of <400° C.

The support for the rhodium and ruthenium metal is spinel $LiAl_5O_8$. The support is usually made by a solution method wherein an aqueous lithium salt is mixed as a solution with alumina followed by drying and calcination typically in air. Calcination is effected at temperatures in the range from 500 to 1500° C., preferably from about 700 to 1000° C. to ensure the $LiAl_5O_8$ composition. Calcination typical requires at least 5 hours, generally from 10 to 25 hours. In formulating the lithium aluminum support, the level of lithium salt is controlled to provide an atomic ratio of lithium/aluminum ratio of from 0.2 to 1.5 to 5.

The lithium aluminate support can also be made by a solid state reaction between a lithium salt and alumina. As with the solution method, the mixture is dried and then calcined at essentially the same high temperatures over extended periods of time. Lithium salts include LiCl, LiBr, LiF, $Li_2O$, $Li_2SO_4$, $LiNO_3$, LiOH, $Li_2CO_3$, $CH_3COOLi$, and HCOOLi with a preference given to $Li_2CO_3$, $LiNO_3$, and CH3COOLi. Source of alumina can be chi-alumina, gamma-alumina, eta-alumina, kappa-alumina, delta-alumina, Theta-alumina and alpha-alumina. For economic reasons, lower cost alumina precursors such as gibbsite, boehmite, bayerite, diaspore, can also be used.

Alkali moderation of the catalyst is a preferred mode of operation. However the lithium aluminate support apparently does not need significant alkali metal hydroxide moderation even with feedstocks having such high levels of oligomer function. A limited amount of alkali metal hydroxide, e.g., lithium hydroxide, 0.1 to 15% (preferred at 0.5% or below based upon catalyst metals) may be employed for effective control of the hydrogenation selectivity.

As with conventional processes, the hydrogenation of methylenedianiline is carried out under liquid phase conditions. Liquid phase conditions are maintained typically by carrying out the hydrogenation in the presence of a solvent. Although as reported in the art, it is possible to effect reaction in the absence of a solvent, the processing usually is much simpler when a solvent is employed. Representative solvents suited for effecting hydrogenation of aromatic amines include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is the preferred solvent.

When a solvent is used, it can be used in concentrations as low as 50% by weight based upon the aromatic amine introduced into the reaction and typically the solvent is used at levels from about 75 to about 200% by weight of the starting compound. Under some circumstances solvent amount as high as 1000 to 2000% based upon the weight of aromatic amine are used.

The reaction temperature range is between 130–210° C., preferably between 170–200° C. The reaction pressure is between 500 and 4000 psig hydrogen, preferably between 700 and 950 psig. The reaction time varies depending on the amount of impurities in the crude MDA but range from one hour to several days. Catalyst levels may range from 0.5 to 5% by weight of the feedstock to be hydrogenated.

The following examples are intended to illustrate various embodiments of the invention and all parts and percentages given are weight parts or weight percents unless otherwise specified.

General Procedure

Feedstock

An MDA-60 feedstock was analyzed by area percent GC using an HP5 column, 25 m long with a 0.17 micron film thickness.

A typical sample of crude MDA-60 employed for evaluation contained, on an area percent basis, 61.3% of the two ring methylenedianiline; 27.6% of the three ring methylene bridged polyphenylamine, and 10.5% of the four ring methylene bridged polyphenylamines (and higher): In addition to the methylenedianiline and oligomers, there was 0.6% (including 0.2% MDA-formamide) of smaller amounts of three or more ring methylene bridged polyphenylamine formamides.

Procedure

The hydrogenation reactions were carried out in a standard 1 L Parr stirred reactor equipped with a 0.5 micron internal filter for catalyst/product separation.

EXAMPLE 1

Hydrogenation of MDA-50 Using Rh/Ru on Lithium Aluminate

A catalyst system consisting of a physical mixture of 4% rhodium by weight on a lithium aluminate support (3.4 g) and 5% ruthenium by weight on lithium aluminate (0.45 g) is charged into the reactor with 200 g tetrahydrofuran. 0.7 g of a 15% solution of lithium hydroxide monohydrate is added, and the catalyst metals are reduced by stirring at 1000 rpm under 850 psig hydrogen at 190° C. for 4 hours. The tetrahydrofuran is filtered out, and 400 g of the MDA-60 feedstock containing approximately 65% of the 2-ring MDA in THF are introduced to the reactor. The MDA is hydrogenated at 185° C. and 800 psig hydrogen, stirred at 1500 rpm until hydrogen uptake stops.

After the reaction was complete, the contents were removed and the catalyst washed and recharged to the reactor. Five uses were carried out to determine the effect of the impurities on catalyst life.

The induction time is recorded separately from the reaction time. It represents the time where there is little to no hydrogen uptake associated with ring hydrogenation. The separate recording of induction and reaction time serves as an important indicator as to whether the respective catalyst system is able to overcome the high concentration of oligomer and formamide impurities such as are present in the MDA-60 feedstock.

Based on GC analysis the hydrogenation of MDA generates partially and fully deaminated PACM, PACM, methylene bridged polycyclohexylalcohols, N-methylated methylene bridged polycyclohexylamines, 3 and 4 ring methylene bridged polycyclohexylamines, and PACM secondary amines (heavies).

COMPARATIVE EXAMPLE 2

Hydrogenation of MDA-50 Using Rh/Ru on Alumina Support

A comparative experiment to that of Example 1 was performed using rhodium and ruthenium on alumina, a commercial catalyst having equivalent ruthenium but slightly higher rhodium content and suited for the hydrogenation of crude methylenedianiline, i.e., MDA-85. The experiment was carried out following the same procedure and using the same reaction conditions except that the catalyst consisted of a mixture of 4% rhodium on alumina (4.5 g) and 5% ruthenium on alumina (0.45 g). Comparative results for Examples 1 and 2 are listed in Tables 1 and 2.

TABLE 1

Hydrogenation Of MDA-50 Using Rhodium And Ruthenium Catalysts Supported On Lithium Aluminate

| Induction time (min) | Reaction time (min) | PACM yield (%) |
|---|---|---|
| 40 | 137 | 61.5 |
| 75 | 225 | 60.0 |
| 132 | 303 | 54.9 |
| 112 | 280 | 51.0 |
| 128 | 348 | 51.3 |

TABLE 2

Hydrogenation Of MDA-50 Using Rhodium And Ruthenium Catalysts Supported On Alumina

| Induction time (min) | Reaction time (min) | PACM yield (%) |
|---|---|---|
| 72 | 247 | 54.8 |
| 240 | 450 | 50.9 |
| 247 | 495 | 46.4 |

Note: the significantly short induction time and reaction times of the usage results in Table 1 compared to Table 2. For example, the second use of the Example 1 catalyst system had a shorter combined induction and reaction time to that of the first use of the rhodium/ruthenium catalyst on alumina. In addition, the yield was approximately 8% higher.

The data also show that the average PACM yield using rhodium/ruthenium metals supported on lithium aluminate catalyst over 3 uses was 58.8% compared to 55.7% for the rhodium/ruthenium catalyst carried on alumina. Over 5 uses the yield was approximately 5% more than the average for rhodium/ruthenium supported on alumina which yield for 3 uses was 50.7%. However, the activity and the robustness of the lithium aluminate based catalyst are significantly better, indicated by the shorter induction/reaction times and higher number of reuses.

COMPARATIVE EXAMPLE 3

Hydrogenation of Distilled MDA

Comparative experiments in accordance with the procedure of Example 2 was done with distilled MDA feed, in which lithium aluminate supported catalyst and alumina supported were employed. Table 3 shows the results.

TABLE 3

The Hydrogenation Of Distilled MDA Using Rhodium And Ruthenium Catalysts Supported On Either Alumina Or Lithium Aluminate

| | Rh/alumina + ruthenium/alumina | | | Rh/li-aluminate + ruthenium/li-aluminate | | |
|---|---|---|---|---|---|---|
| Use | Induction time (min) | Reaction time (min) | PACM yield (%) | Induction time (min) | Reaction time (min) | PACM yield (%) |
| 1 | 0 | 238 | 71.1 | 0 | 189 | 75.2 |
| 2 | 0 | 160 | 76.0 | 6 | 170 | 76.3 |
| 3 | 0 | 120 | 83.1 | 6 | 160 | 78.0 |

The results show that there is no substantial difference with respect to the catalyst performance in hydrogenating distilled MDA, whether the metals are supported on lithium aluminate or alumina in terms of activity and induction time. In contrast, Example 1 shows that the lithium aluminate support provides an unexpected difference in catalyst performance when hydrogenating a high oligomers feedstock, i.e., MDA-60.

Note: this comparison clearly indicates that there is little difference in activity/selectivity between the alumina supported and lithium aluminate supported catalysts for hydrogenation of oligomer free (distilled) MDA.

The difference in activity of these two catalysts, indicated by induction time and reaction time with regard to the hydrogenation of MDA-60 as demonstrated in Table 1 and Table 2 is unexpected.

EXAMPLE 4

Hydrogenation of MDA-60 Pretreated with Ruthenium/Li-Aluminate Catalyst

This example shows a two step reaction where the MDA-60 feedstock was first pretreated with a ruthenium/li-aluminate catalyst, and then, the pretreated feedstock hydrogenated in the presence of the Example 1 catalyst system consisting of a physical mixture of rhodium/li-aluminate with ruthenium/li-aluminate.

More specifically, the Step 1 pretreatment was carried out using an MDA-60 feed in THF (65/35, w/w). 500 g of the feed was stirred in the presence of 1.0 g ruthenium(5%)/li-aluminate at 185° C. and 800 psig $H_2$ for 100 minutes. This pretreated feedstock was then used as the feed in step 2.

Step 2: The hydrogenation of the pretreated MDA feedstock was carried out using a catalyst consisting of Rh(4%)/li-aluminate (4.3 g) and ruthenium/li-aluminate (0.48 g).

The reaction temperature was 185° C. and the hydrogen pressure was 800 psig. Results for 5 consecutive uses of the same catalyst are listed in Table 4:

TABLE 4

The Hydrogenation Of Pretreated MDA Feed With Rhodium And Ruthenium Catalysts Supported On Lithium Aluminate

| Use | Pretreatment time (min) | Reaction time (min) | PACM yield (%) |
|---|---|---|---|
| 1 | 100 | 250 | 68.6 |
| 2 | 100 | 227 | 65.1 |
| 3 | 100 | 177 | 67.1 |
| 4 | 100 | 174 | 65.7 |
| 5 | 100 | 201 | 65.0 |

Note: these results demonstrate the unexpected robustness of lithium-aluminate supported rhodium/ruthenium catalyst system in the ring hydrogenation of an MDA feed with high level of oligomers and poisons. This 2 step process will allow even better catalyst life and higher yields. Also, excellent catalyst stability against feed poisons was observed over the five uses.

The invention claimed is:

1. In a process for the catalytic hydrogenation of methylenedianiline to its ring hydrogenated counterparts, by contacting the methylenedianiline with hydrogen in the presence of a catalyst system comprised of rhodium and ruthenium carried on a support, the improvement which comprises:
   utilizing a methylenedianiline feedstock having at least 40% by weight of polycyclic oligomer impurities, and,
   effecting the hydrogenation in the presence of a catalyst system comprised of rhodium and ruthenium carried on a lithium aluminate support.

2. The process of claim 1 wherein the weight ratio of rhodium to ruthenium in the catalyst system is from 1 to 20 weight parts rhodium per weight part of ruthenium.

3. The process of claim 2 wherein the weight of rhodium to lithium aluminate support is from 2 to 8 weight parts per 100 weight parts lithium aluminate support plus metal.

4. The process of claim 3 wherein the weight of ruthenium to lithium aluminate is from 2 to 8 to weight parts per 100 weight parts lithium aluminate support.

5. The process of claim 4 wherein the catalyst system is a physical mixture of rhodium on lithium aluminate and ruthenium on lithium aluminate.

6. The process of claim 5 wherein weight ratio of rhodium to ruthenium in the catalyst system is from 6 to 15 weight parts rhodium per weight part of ruthenium.

7. The process of claim 6 wherein the feedstock is selected from the group consisting of MDA-50 and MDA-60.

8. The process of claim 7 wherein the hydrogenation pressure is from 200 to 4000 psig.

9. In a process for the catalytic hydrogenation of methylenedianiline to its ring hydrogenated counterparts, by contacting the methylenedianiline with hydrogen in the presence of a catalyst system comprised of rhodium and ruthenium carried on a support, the improvement which comprises:
   utilizing a methylenedianiline feedstock having at least 40% by weight of polycyclic oligomers and at least 0.2% by weight of formamide byproducts,
   prereacting the methylenedianiline feedstock in the presence of a catalyst comprised of ruthenium carried on a lithium aluminate support; and
   effecting the hydrogenation of the prereacted methylenedianiline feedstock in the presence of a catalyst system comprised of rhodium and ruthenium carried on a lithium aluminate support.

10. The process of claim 9 wherein the weight of rhodium to lithium aluminate support is from 2 to 8 weight parts per 100 weight parts lithium aluminate support plus metal.

11. The process of claim 10 wherein the weight of ruthenium to lithium aluminate is from 2 to 8 to weight parts per 100 weight parts lithium aluminate support.

12. The process of claim 11 wherein the catalyst system is a physical mixture of rhodium on lithium aluminate and ruthenium on lithium aluminate.

13. The process of claim 12 wherein weight ratio of rhodium to ruthenium in the catalyst system is from 6 to 15 weight parts rhodium per weight part of ruthenium.

14. The process of claim 13 wherein the feedstock is selected from the group consisting of MDA-50 and MDA-60.

* * * * *